(12) United States Patent
Gasco

(10) Patent No.: US 6,419,949 B1
(45) Date of Patent: Jul. 16, 2002

(54) MICROPARTICLES FOR DRUG DELIVERY ACROSS MUCOSA AND THE BLOOD-BRAIN BARRIER

(76) Inventor: Maria Rosa Gasco, Lungo Po Antonelli, 207, Torino (IT)

( * ) Notice: Subject to any disclaimer, the term of this patent is extended or adjusted under 35 U.S.C. 154(b) by 0 days.

(21) Appl. No.: 09/555,828
(22) PCT Filed: Nov. 27, 1998
(86) PCT No.: PCT/EP98/07664
§ 371 (c)(1), (2), (4) Date: Jun. 1, 2000
(87) PCT Pub. No.: WO99/27918
PCT Pub. Date: Jun. 10, 1999

(30) Foreign Application Priority Data

Dec. 1, 1997 (IT) .......................... MI97A2663

(51) Int. Cl.[7] ............................... A61K 9/127
(52) U.S. Cl. ................ 424/450; 424/456; 424/489; 514/937; 514/941
(58) Field of Search ............... 424/450, 456, 424/489; 514/937, 941

(56) References Cited

U.S. PATENT DOCUMENTS 5,858,398 A * 1/1999 Cho et al. ............... 424/450

FOREIGN PATENT DOCUMENTS

| DE | 3421468 | 12/1985 | |
| DE | 4131562 | 3/1993 | .......... A61K/9/127 |
| EP | 0167825 | 1/1986 | .......... A61K/9/50 |
| EP | 526666 | 2/1993 | .......... A61K/9/51 |
| WO | 9505164 | 2/1995 | .......... A61K/9/14 |
| WO | WO9505164 | 2/1995 | .......... A61K/9/14 |
| WO | 9856362 | 12/1998 | .......... A61K/9/51 |
| WO | 9927918 | 6/1999 | .......... A61K/9/51 |

OTHER PUBLICATIONS

Kreuter, "Passage of Peptides through the Blood–Brain Barrier with Colloidal Polymer Particles (Nanoparticles)", *Brain Research* 674 (1995) 171–174.

* cited by examiner

Primary Examiner—Deborah D. Carr

(57) ABSTRACT

Pharmaceutical composition comprising micro particles having an average diameter ranging from 40 to 150 nm, consisting of one or more lipids, a drug and, optionally, a steric stabilizer, suitable to the transmucosal passage and to the overcoming of the blood-brain barrier and the blood-cerebrospinal fluid barrier, said micro particles being obtained dispersing in an aqueous medium cooled to 2–4° C. an oil/water or a water/oil/water micro emulsion comprising said constituents.

7 Claims, No Drawings

MICROPARTICLES FOR DRUG DELIVERY ACROSS MUCOSA AND THE BLOOD-BRAIN BARRIER

This application is a 371 of PCT/EP98/07644 filed Nov. 27, 1998.

PRIOR ART

An important problem in the field of the administration and the absorption of drugs consists of the difficulty of the passage for some drugs through the intestinal mucosa and of the difficulty of the passage through the blood-brain barrier and the blood-cerebrospinal fluid barrier.

In fact the drugs administered by mouth and destined to pass through the intestinal mucosa find a limitation due to the gastrointestinal pH, to the residence time and to the solubility.

For example biodegradable drugs such as proteins and peptides, and slightly soluble drugs such as some cytostatics are not suitable for this kind of administration.

On the other hand drugs as the peptides or the antibiotics such as ampicillin and the anti-tumour drugs such as the cyclophosphamide are not able to pass through the blood-brain barrier.

Several researches on the absorption of the colloidal polymeric particles of polystyrene, polyglycol lactates, polyalkilcyanoacrylates ansacrylates and of polymeric liposomes as carriers of drugs by the gastrointestinal tract after the administration by mouth have been carried out and the passage of said particles through the intestinal mucosa has been proved.

The results of said researches are described for example by A. T. Florence, The Oral Absorption of Micro- and Nanoparticulates:

Neither Exceptional, Not Unusual, Pharm. Res. 14, 259 (1997) and by H. Chen, V. Torchilin, R. Langer, Polymerized Liposomes as Potential Oral Vaccine: Stability and Bioavailability, J. Controlled Release. 42, 263 (1996).

However said colloidal particles have the drawback of a very low passage. Moreover the polymers contain traces of solvents and degradation products which are not pharmaceutically acceptable.

Finally the polystyrene is not acceptable because it is not biodegradable.

As far as the preparation of compositions suitable to the passage through the blood-brain barrier is concerned, nanoparticles of polybutylcyanoacrylate containing drugs such as the gentamicin, administered by intravenous way in rats have been used obtaining very partial results. More often one resorts to the implantation of the carriers in the skull in the case of brain cancers (Menei P. et al., Neurosurgery 39, 117 (1996)).

SUMMARY

Pharmaceutical compositions in the form of microparticles suitable to the passage through the intestinal mucosa, the blood-brain barrier and the blood-cerebrospinal fluid barrier have been now found.

Said microparticles have a size ranging from 40 to 150 nm, they are formed by one or more lipids optionally in combination with a steric stabilizer and by a drug.

Said microparticles are prepared dispersing in an aqueous medium at 2–4° C. a hot prepared oil/water or water/oil/water microemulsion comprising one or more lipids, a surfactant agent, a cosurfactant agent and optionally a steric stabilizer.

DETAILED DESCRIPTION OF THE INVENTION

The characteristics and the advantages of the pharmaceutical compositions in the form of microparticles suitable to the passage through the intestinal mucosa, the blood-brain barrier and the blood-cerebrospinal fluid barrier according to the present invention will be mostly shown during the following description.

Said microparticles are obtained dispersing in an aqueous medium cooled at 2–4° C. an oil/water or water/oil/water microemulsion prepared according to the following description.

The preparation by the oil/water microemulsion is carried out by the following steps:

a) a mixture consisting of one or more lipids, at least a surfactant agent and at least a cosurfactant agent is warmed at a temperature at least equal to the melting temperature of the lipids;

b) a mixture consisting of a drug dissolved or dispersed in water and optionally a steric stabilizer, warmed at a temperature at least equal to the temperature of the step a) is added to said mixture of step a), obtaining an oil/water microemulsion;

c) the microemulsion is dispersed in an aqueous medium at 2–4° C. obtaining the microparticles in suspension;

d) the microparticles suspension is washed by an aqueous medium by diafiltration and freeze-dried.

The preparation by the water/oil/water microemulsion is carried out by the following steps:

a') a mixture consisting of one or more lipids, at least a surfactant agent and at least a cosurfactant agent is warmed at a temperature at least equal to the melting temperature of the lipids;

b') a mixture consisting of a drug dissolved or dispersed in water warmed at a temperature at least equal to the temperature of the step a') is added to the mixture of step a') obtaining a water/oil microemulsion;

c') a mixture consisting of water, at least a surfactant agent and at least a cosurfactant agent and optionally a steric stabilizer warmed at a temperature at least equal to the temperature of the step a') is added to said microemulsion obtaining the water/oil/water microemulsion;

d') said water/oil/water microemulsion is dispersed in an aqueous medium at 2–4° C. obtaining the microparticles in suspension;

e') the microparticles suspension is washed by water by diafiltration and freeze-dried.

The amount of water used in the steps c) and d') is ranging from 5 to 200 volumes per volume of the respective microemulsion.

The obtained microparticles have an average diameter ranging from 40 to 150 nm and preferably from 60 to 100 nm and a polydispersion index ranging from 0.15 to 0.28.

The lipids used in the preparation of the microparticles according to the present invention are selected from the group consisting of the stearic acid, the palmitic acid, the triglycerides, the diglycerides and the monoglycerides.

The surfactant agents are selected among soy-bean phosphatidylcholine, dioleyl phosphatidylcholine, dipalmitoyl phosphatidylcholine, hydrogenated soy-bean phosphatidylcholine, phosphatidylethanolamine and phosphatidylserine.

The cosurfactant agents are selected among ethanol, propanol, isopropanol, butanol, sodium taurocholate, sodium glycocholate, propylene glycol, butyric acid and benzoic acid.

The possible steric stabilizer is selected among dipalmitoyl phosphatidyl ethanolamine-PEG, PEG-stearate, the esters of the fatty acids from the myristic acid to the docosanoic acid with methyl ether PEG, the diacylphosphatidyl ethanolamines esterified with methyl ether PEG and the polylactates and the polyglycolactates esterified with methyl ether PEG.

The methyl ether PEG has preferably a molecular weight ranging from 750 to 2000.

The washing by diafiltration of the steps d) and e') has the aim to remove the surfactant agent, the cosurfactant agent and the possible drug not included in the lipid so that the final composition of the microparticles results:

lipids, from 80 to 99% by weight, drug, from 1 to 20% by weight, or:

lipids, from 75 to 98.5% by weight, steric stabilizer, from 0.5 to 15% by weight, drug, from 1 to 10% by weight.

The microparticles according to the present invention are successfully used in the preparation of the compositions suitable to the administration by mouth for the transmucosal absorption directed towards the lymphatic system and for the intravenous administration for the overcoming of the blood-brain barrier and the blood-cerebrospinal fluid barrier.

The compositions containing the steric stabilizer are particularly suitable for the intravenous administration.

Forms suitable to the administration by mouth are aqueous dispersions, having a microparticle content ranging from 20 to 200 mg/ml.

Forms suitable to the intravenous administration are aqueous dispersions having a microparticle content ranging from 30 to 150 mg/ml.

Drugs particularly suitable for the transmucosal way are cytostatic drugs used for the therapy of the lymphomas such as methotrexate, hydarubicin, cyclophosphamide, vincristine and vinblastine, antibiotics such as the gentamicin and peptides such as calcitonin, LHRH and analogous ones.

Drugs particularly suitable for the passage of the blood-brain barrier and the blood-cerebrospinal fluid barrier are the peptides such as LHRH and analogous ones, enkephalins, antibiotics such as ampicillin and gentamicin and anti-tumour drugs such as the cyclophosphamide and derivatives, carmustine and carboplatinum.

As far as the transmucosal transport is concerned we have the advantage that the transport by lymphatic way avoids the first passage through the liver, it allows the administration by mouth of drugs, such as lipids, for which such administration is not always possible and it allows the treatment of the lymphatic system cancers.

As far as the transport through the blood-brain barrier and the blood-cerebrospinal fluid barrier is concerned, the compositions according to the present invention allow the passage of drugs included in the carriers which normally do not pass or pass in an insufficient amount to obtain a suitable therapeutic effect.

Pharmacological Experimentation

Radio-labelled microparticles have been prepared acting according to the Example 3, reported below, and adding a solution of 131 iodoheptadecanoic acid to the warm oil/water microemulsion.

The experimentation has been carried out in male albin rats of a Wistar strain (Charles River-Italy) having a weight equal to 550–650 g.

Doses equal to 10 mg/kg (about 40 $\mu$Ci) of an aqueous dispersion of microparticles have been administered at the duodenal level to different groups of rats.

Samples of lympha from the thoracic duct and blood from the jugular vein have been taken at different times.

The data are reported in the Table 1 wherein the radioactivity percentage is reported with respect to the dose administered per gram of lympha and per gram of blood as a function of the time.

TABLE 1

Average values of radioactivity percentage of the administered dose per gram of lympha (A) or of blood (B) determined in time by gamma counting.

| Time after the administration | A radioactivity %/Lympha g. | B radioactivity %/Blood g. |
| --- | --- | --- |
| 30' | 1 | 0.09 |
| 60' | 1.5 | 0.08 |
| 90' | 3 | 0.08 |
| 120' | 9 | 0.07 |
| 150 | 8 | 0.07 |
| 180 | 7.5 | 0.07 |

The same dispersion has been administered by intravenous way to the rats (10 mg/kg) (about 30 $\mu$Ci). The passage through the blood-brain barrier is pointed out by the presence in the liquor of about 5% of the total radioactivity after 10 minutes from the administration.

For illustrative aim the following Examples of microparticles preparations according to the present invention are reported.

EXAMPLE 1 a) A mixture consisting of 180 mg of stearic acid, 92 mg of phosphatidylcholine, 12 mg of dioleyl phosphatidylcholine, 72 mg of butanol and 16 mg of butyric acid is warmed at 70° C.

b) 28 mg of an aqueous solution of LHRH (40 mg/ml) warmed at 70° C., are added under stirring to the mixture of the step a) obtaining a water/oil microemulsion;

c) A mixture consisting of 274.4 mg of water, 16.8 mg of soy-bean phosphatidylcholine, 20.8 mg of butanol, 32.4 mg of sodium taurocholate and 4.0 mg of butyric acid, warmed at 70° C., is added under stirring to 52 mg of the water/oil microemulsion of the step b) obtaining a water/oil/water microemulsion.

d) The water/oil/water microemulsion of the step c) is dispersed in a ratio equal to 1:10 in water at a temperature equal to 2–3° C. obtaining the microparticles in an aqueous dispersion.

e) The aqueous dispersion of the step d) is washed three times with water by diafiltration and subsequently it is freeze-dried.

The following results are obtained:

drug incorporated in the microparticles: 80%;

average diameter of the microparticles.: 96 nm;

polydispersion index: 0.23.

EXAMPLE 2

A mixture consisting of 273.6 mg of water, 16.4 mg of phosphatidylcholine, 20.0 mg of butanol, 32.0 mg of sodium taurocholate, 2.4 mg of butyric acid and 2.8 mg of dipalmitoyl phosphatidyl ethanolamine-PEG (steric stabilizer), warmed at 70° C., is added under stirring to 52.0 mg of the water/oil microemulsion of the step b) of the Example 1.

The preparation is completed according to the steps d) and e) of the Example 1.

The following results are obtained:

drug incorporated in the microparticles: 78%;

average diameter of the microparticles: 100 nm;

polydispersion index: 0.24.

EXAMPLE 3 a) A mixture consisting of 24 mg of stearic acid and 6.0 mg of monostearine is warmed at 70° C.;

b) a mixture consisting of 6.0 mg of gentamicin, 56.0 mg of sodium taurocholate, 28.0 mg of soy-bean phosphatidylcholine and 280.0 mg of water, warmed at 70° C., is added under stirring to the mixture of the step a) obtaining an oil in water microemulsion.

The microemulsion obtained in the step b) is then treated as described in the steps d) and e) of the Example 1.

The following results are obtained:

gentamicin incorporated in the microparticles: 80%;

average diameter of the microparticles: 105 nm;

polydispersion index: 0.22.

EXAMPLE 4 a) A mixture consisting of 210.0 mg of stearic acid, 10.0 mg of monostearine, 62.0 mg of soy-bean phosphatidylcholine, 80.0 mg of butyric acid and 6.0 mg of butanol is warmed at 70° C.

b) 36.0 mg of an aqueous solution of calcitonin (2 mg/ml) warmed at 68° C. are added to the mixture of the step a) obtaining a water/oil microemulsion.

c) A mixture consisting of 214.4 mg of water, 16.8 mg of soy-bean phosphatidylcholine, 16.4 g of butyric acid, 8.0 g of butanol and 32.4 g of sodium taurocholate, warmed at 70° C., is added under stirring to 52.0 mg of the water/oil microemulsion of the step b), obtaining a water/oil/water microemulsion.

The preparation is then completed working according to the steps d) and e) of the Example 1.

The following results are obtained:

incorporation of the calcitonin: 83%;

average diameter of the microparticles: 93 nm;

polydispersion index: 0.23.

EXAMPLE 5

A mixture consisting of 212.4 mg of water, 16.8 mg of soy-bean phosphatidylcholine, 16.4 mg of butyric acid, 8.0 g of butanol, 32.4 mg of sodium taurocholate and 8.0 mg of stearic acid-PEG (steric stabilizer) warmed at 68° C. is added under stirring to 52.0 mg of the water/oil microemulsion of the step b) of the Example 4.

The preparation is completed according to the steps d) and e) of the Example 1.

The following results are obtained:

incorporation of the calcitonin: 70%;

average diameter of the microparticles: 102 nm;

polydispersion index: 0.23.

What is claimed is:

1. Compositions suitable to oral administration for transmucosal absorption and to intravenous administration for overcoming of the blood-brain barrier and the blood-cerebrospinal fluid barrier, comprising aqueous dispersions of microparticles having an average diameter ranging from 40 to 150 nm and a polydispersion index ranging from 0.15 to 0.28, said microparticles consisting of one or more lipids, a drug and, optionally, a stabilizing agent selected from the group consisting of dipalmitoyl phosphatidyl ethanolamine-PEG, PEG-stearate, esters of the fatty acids from myristic acid to docosanoic acid with methyl ether PEG, diacylphosphatidyl ethanolamines esterified with methyl ether PEG and polylactates and polyglycolactates esterified with methyl ether PEG, said microparticles prepared by dispersing in an aqueous medium, cooled at 2 to 4° C., an oil in water or a water/oil/water microemulsion warmed at a temperature near the melting temperature of the lipids, washing with water by diafiltration and freeze-drying.

2. Compositions as claimed in claim 1, wherein said microparticles are present in said aqueous dispersions in an amount ranging from 20 to 200 mg/ml.

3. Compositions as claimed in claim 1, wherein said microparticles consist of one or more lipids in an amount ranging from 80 to 99% by weight and of a drug in an amount ranging from 1 to 20% by weight.

4. Compositions as claimed in claim 1, wherein said microparticles consist of one or more lipids in an amount ranging from 75 to 98.5% by weight, of said stabilizing agent in an amount ranging from 0.5 to 15% by weight and of a drug in an amount ranging from 1 to 10% by weight.

5. Compositions as claimed in claim 1, wherein said lipids are selected from the group consisting of stearic acid, palmitic acid, triglycerides, diglycerides and monoglycerides.

6. Compositions as claimed in claim 1, wherein said drug is selected from the group consisting of methotrexate, hydarubicin, cyclophosphamide, vincristine, vinblastine, gentamicin, calcitonin, LHRH, enkephalins, ampicillin, gentamicin, carmustine and carboplatinum.

7. Compositions as claimed in claim 1, wherein said microparticles are obtained by dispersing, in an aqueous medium cooled at 2–4° C., an oil in water or a water/oil/water microemulsion warmed at a temperature near the melting temperature of the lipids, washing with water by diafiltration and freeze-drying.

* * * * *